(12) United States Patent
Harrison et al.

(10) Patent No.: US 11,568,174 B2
(45) Date of Patent: Jan. 31, 2023

(54) CO-HETEROGENEOUS AND ADAPTIVE 3D PATHOLOGICAL ABDOMINAL ORGAN SEGMENTATION USING MULTI-SOURCE AND MULTI-PHASE CLINICAL IMAGE DATASETS

(71) Applicant: Ping An Technology (Shenzhen) Co., Ltd., Shenzhen (CN)

(72) Inventors: Adam P Harrison, Bethesda, MD (US); Ashwin Raju, Bethesda, MD (US); Yuankai Huo, Bethesda, MD (US); Jinzheng Cai, Bethesda, MD (US); Le Lu, Bethesda, MD (US)

(73) Assignee: PING AN TECHNOLOGY (SHENZHEN) CO., LTD., Shenzhen (CN)

( * ) Notice: Subject to any disclaimer, the term of this patent is extended or adjusted under 35 U.S.C. 154(b) by 209 days.

(21) Appl. No.: 17/089,257

(22) Filed: Nov. 4, 2020

(65) Prior Publication Data
US 2021/0256315 A1 Aug. 19, 2021

Related U.S. Application Data

(60) Provisional application No. 62/977,906, filed on Feb. 18, 2020.

(51) Int. Cl.
*G06K 9/00* (2022.01)
*G06K 9/62* (2022.01)
(Continued)

(52) U.S. Cl.
CPC ......... *G06K 9/6259* (2013.01); *G06K 9/6265* (2013.01); *G06T 7/0012* (2013.01);
(Continued)

(58) Field of Classification Search
CPC .. G06K 9/6259; G06K 9/6265; G06T 7/0012; G06T 7/11; G06T 2207/20081;
(Continued)

(56) References Cited

U.S. PATENT DOCUMENTS 10,430,946 B1 * 10/2019 Zhou .................. A61B 5/02007
2019/0259153 A1 * 8/2019 Zhang .................... G06V 10/82
(Continued)

*Primary Examiner* — Van D Huynh
(74) *Attorney, Agent, or Firm* — Anova Law Group, PLLC

(57) ABSTRACT

The present disclosure describes a computer-implemented method for processing clinical three-dimensional image. The method includes training a fully supervised segmentation model using a labelled image dataset containing images for a disease at a predefined set of contrast phases or modalities, allow the segmentation model to segment images at the predefined set of contrast phases or modalities; finetuning the fully supervised segmentation model through co-heterogenous training and adversarial domain adaptation (ADA) using an unlabelled image dataset containing clinical multi-phase or multi-modality image data, to allow the segmentation model to segment images at contrast phases or modalities other than the predefined set of contrast phases or modalities; and further finetuning the fully supervised segmentation model using domain-specific pseudo labelling to identify pathological regions missed by the segmentation model.

20 Claims, 10 Drawing Sheets

(51) Int. Cl.
*G06T 7/00* (2017.01)
*G06T 7/11* (2017.01)
*G16H 30/40* (2018.01)
*G06V 10/46* (2022.01)

(52) U.S. Cl.
CPC .............. *G06T 7/11* (2017.01); *G06V 10/462* (2022.01); *G16H 30/40* (2018.01); *G06T 2207/20081* (2013.01); *G06T 2207/20084* (2013.01); *G06T 2207/30056* (2013.01); *G06V 2201/031* (2022.01)

(58) Field of Classification Search
CPC . G06T 2207/20084; G06T 2207/30056; G06T 2207/10076; G06T 2207/10081; G06T 2207/30096; G06T 7/0016; G06V 10/462; G06V 2201/031; G06V 10/764; G06V 20/64; G16H 30/40; G16H 20/40; G16H 50/50; G16H 50/20
USPC ........................................................ 382/128
See application file for complete search history.

(56) References Cited

U.S. PATENT DOCUMENTS

| | | | |
|---|---|---|---|
| 2020/0234448 A1* | 7/2020 | Dai | G06K 9/6298 |
| 2020/0311911 A1* | 10/2020 | Poole | G16H 50/20 |
| 2021/0150710 A1* | 5/2021 | Hosseinzadeh Taher | G06V 10/82 |
| 2021/0209418 A1* | 7/2021 | Badanes | G06K 9/6292 |
| 2021/0233247 A1* | 7/2021 | Cao | G06N 3/08 |
| 2021/0248736 A1* | 8/2021 | Kamen | G06T 7/0012 |
| 2021/0383538 A1* | 12/2021 | Deasy | G06T 7/11 |

* cited by examiner

CO-HETEROGENEOUS AND ADAPTIVE 3D PATHOLOGICAL ABDOMINAL ORGAN SEGMENTATION USING MULTI-SOURCE AND MULTI-PHASE CLINICAL IMAGE DATASETS

CROSS-REFERENCE TO RELATED APPLICATIONS

This application claims the priority of U.S. Provisional Patent Application No. 62/977,906, filed on Feb. 18, 2020, the entire content of which is incorporated herein by reference.

THE FIELD OF THE DISCLOSURE

The present disclosure generally relates to the field of image processing and, more particularly, relates to methods, systems, and computer program products for image processing using a co-heterogenous and adaptive segmentation-based strategy.

BACKGROUND

Segmenting or delineating anatomical structures is an important task within medical imaging, e.g., to generate biomarkers, quantify or track disease progression, or to plan radiation therapy. Manual delineation is prohibitively expensive, which has led to a considerable body of work on automatic segmentation. However, a perennial problem in medical imaging is that models trained on available image/mask pairs, e.g., publicly available data, do not always reflect clinical conditions upon deployment, e.g., different pathologies, patient characteristics, scanners, and imaging protocols. This can lead to potentially drastic performance gaps. When multi-modality or multi-phase imagery is present, e.g., dynamic-contrast multi-phase computed tomography (CT), these challenges are further compounded, as datasets may differ in their composition of available modalities or each may even themselves consist of heterogeneous combinations of modalities. The challenges then are in both managing new patient/disease variations and in harmonizing heterogeneous multi-phase/multi-modality data.

Accordingly, there is a need to design more appropriate strategies for learning-based auto-segmentation methods in order to improve segmentation performance on medical images in radiation therapy or related fields.

BRIEF SUMMARY OF THE DISCLOSURE

According to one aspect of the present disclosure, a computer-implemented method for processing clinical three-dimensional image is provided. The method includes training a fully supervised segmentation model using a labelled image dataset containing images for a disease at a predefined set of contrast phases or modalities, to allow the segmentation model to segment images at the predefined set of contrast phases or modalities; finetuning the fully supervised segmentation model through co-heterogenous training and adversarial domain adaptation (ADA) using an unlabelled image dataset containing clinical multi-phase or multi-modality image data, to allow the segmentation model to segment images at contrast phases or modalities other than the predefined set of contrast phases or modalities; and further finetuning the fully supervised segmentation model using domain-specific pseudo labelling to identify pathological regions, e.g., lesions, missed by the segmentation model.

According to another aspect of the present disclosure, a computer program product for processing clinical three-dimensional image is provided. The computer program product includes a non-transitory computer readable storage medium and program instructions stored therein, where the program instructions are configured to be executable by a computer to cause the computer to perform operations including training a fully supervised segmentation model using a labelled image dataset containing images for a disease at a predefined set of contrast phases or modalities, allow the segmentation model to segment images at the predefined set of contrast phases or modalities; finetuning the fully supervised segmentation model through co-heterogenous training and ADA using an unlabelled image dataset containing clinical multi-phase or multi-modality image data, to allow the segmentation model to segment images at contrast phases or modalities other than the predefined set of contrast phases or modalities; and further finetuning the fully supervised segmentation model using domain-specific pseudo labelling to identify pathological regions missed by the segmentation model.

According to yet another aspect of the present disclosure, a system for processing clinical three-dimensional image is provided. The system includes a processor and a non-transitory memory containing computer program instructions that are configured to be executed by the processor to perform operations training a fully supervised segmentation model using a labelled image dataset containing images for a disease at a predefined set of contrast phases or modalities, allow the segmentation model to segment images at the predefined set of contrast phases or modalities; finetuning the fully supervised segmentation model through co-heterogenous training and ADA using an unlabelled image dataset containing clinical multi-phase or multi-modality image data, to allow the segmentation model to segment images at contrast phases or modalities other than the predefined set of contrast phases or modalities; and further finetuning the fully supervised segmentation model using domain-specific pseudo labelling to identify pathological regions missed by the segmentation model.

Other embodiments of one or more of these aspects and other aspects include corresponding apparatus, and computer programs, configured to perform the various actions and/or store various data described in association with these aspects. Numerous additional features may be included in these and various other embodiments, as discussed throughout this disclosure.

It should be understood that the language used in the present disclosure has been principally selected for readability and instructional purposes, and not to limit the scope of the subject matter disclosed herein.

BRIEF DESCRIPTION OF THE DRAWINGS

The accompanying drawings, which are incorporated in and constitute a part of the specification, illustrate various embodiments of the present disclosure and, together with the description, serve to explain the principles of the present disclosure.

DETAILED DESCRIPTION

Figure 1:
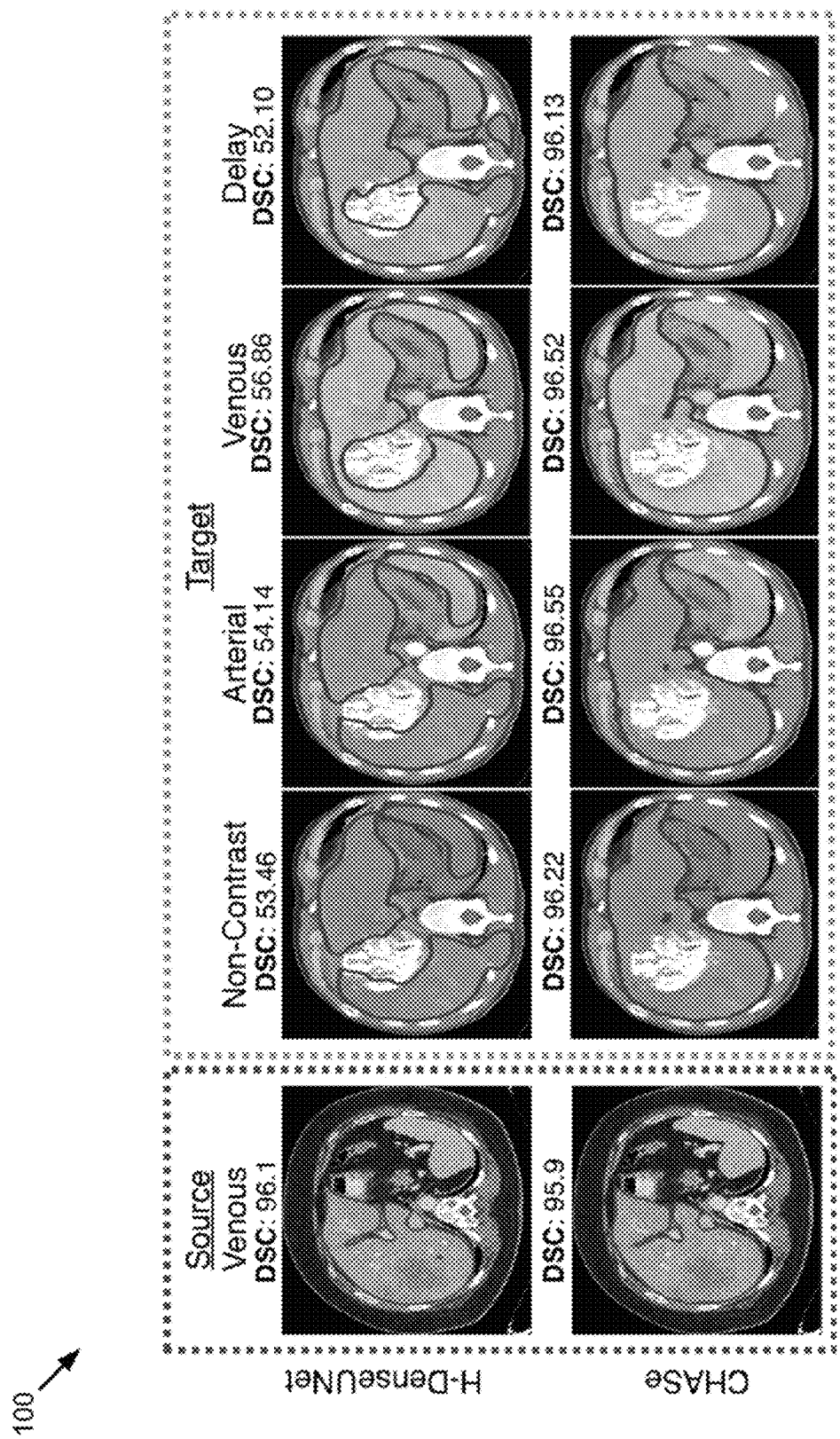
FIG. 1 illustrates an exemplary performance of a CHASe-based segmentation model, according to some embodiments of the present disclosure.

While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be interpreted as open ended, such that an item or items following any one of these words is not meant to be an exhaustive listing of the item or items, or meant to be limited to only the listed item or items. And the singular forms "a," "an," and "the" are intended to include plural references, unless the context clearly dictates otherwise.

Systems and methods consistent with the present disclosure are directed to segmenting a medical image using learning algorithms. As used herein, a "learning algorithm" refers to any algorithm that can learn a model or a pattern based on existing information or knowledge. For example, the learning algorithm may be a machine learning algorithm or any other suitable learning algorithm. In some embodiments, a supervised learning algorithm, such as a full convolutional network (FCN), U-Net or V-Net style encoder/decoders, deeply supervised progressive holistically nested network (PHNN) may be used. In some other embodiments, semi-supervised learning algorithms may also be used.

Supervised learning is a branch of machine learning that infers a predication model given a set of training data. Each individual sample of the training data is a pair containing a data vector (such as a series of measurements) and a desired output value. A supervised learning algorithm analyzes the training data and produces a predictor function. The predictor function is called a classifier or a classification model when the output is discrete, such as a list of labels identifying different groups. The predictor function, once derived through training, is capable of predicting the correct output value for any valid input object.

Semi-supervised learning considers the problem of classification when only a small subset of the observations have corresponding class labels. Such problems are of immense practical interest in a wide range of applications, including image search, genomics, natural language parsing, and speech analysis, where unlabelled data is abundant, but obtaining class labels is expensive or impossible to obtain for the entire data set. The semi-supervised learning addresses how can properties of the data be used to improve decision boundaries and to allow for classification that is more accurate than that based on classifiers constructed using the labelled data alone.

Consistent with the disclosed embodiments, image segmentation may be formulated as a learning-based classification function, which classifies each image point of the medical image into one of the anatomical structures. As used herein, an "image point" refers to an image element in a digital image that corresponds to a physical point in the underlying object. For example, the image point is a pixel in a 2D image or a voxel in a 3D image.

Consistent with the disclosed embodiments, the image segmentation may also classify image blocks rather than image points. As used herein, an "image block" is a group of image points to be classified together. For example, the image block may be a super-pixel in a 2D image, or a super-voxel in a 3D image. When image points within an image block are known to belong to the same anatomical structure, classifying based on image blocks may be more efficient and accurate.

The disclosed segmentation methods generally include two stages: a training stage that "trains" or "learns" an anatomical classification model, and a classification stage that uses the anatomical classification model to predict the anatomical structure that each image point/image block belongs to.

Consistent with the disclosed embodiments, the training process uses a set of training images to learn the anatomical classification model. In some embodiments, a "training image" is an image where the image points are already classified and labelled. For example, a training image may be previously curated or labelled. Therefore, image points in the training image are associated with known anatomical structures. In some embodiments, a "training image" is an image that is not classified or labelled.

Consistent with the disclosed embodiments, one part of the training process in a semi-supervised training uses the landmark features of each image point as the training data vector, and the known anatomical label of the corresponding image point as the desired output, and applies the supervised learning algorithm. Another part of the training process in a semi-supervised training improve decision boundaries and to allow for classification that is more accurate than that based on classifiers constructed using the labelled data alone. Once properly trained using different processes, such an algorithm can be used as part of an anatomical classifier.

Consistent with the disclosed embodiments, the classification module uses the trained classifier to make predictions regarding anatomical structures of image points in a medical image that has not been segmented. In the machine learning context, the classification is only a prediction of which anatomical structure the image point most likely belongs to. In other words, the classification module determines the probabilities that a particular image point belongs to each anatomical structure, and then predicts that the image point should belong to the anatomical structure associated with the highest probability.

Consistent with the disclosed embodiments, the classification module also identifies landmark points on the medical image to be segmented, and determines landmark features of each image point in the image based on these landmark points. The landmark points are generally at the same locations as those identified on the training images. Similarly, the landmark features determined are also generally of the same types as those determined during the training process. The landmark features are then provided to the trained classifier to yield predictions of an anatomical structure label for each image point. Once all the image points in the medical image are properly labelled, the image has been segmented. For instance, a supervised training module trained with a curated and labelled dataset at a specific contrast phase (e.g., a venous (V)-phase for liver CT scans and masks) or modality may allow prediction of that specific stage or modality from the image data.

Consistent with the disclosed embodiments, the training module and the classification module may also be further finetuned through semi-supervised learning, such as co-training. For instance, an appearance-based semi-supervision may be applied by fusing co-training with hetero-modality learning (together may be referred to as "co-heterogenous learning"), to finetune the training module and the classification module. This allows the predictions of certain unlabelled data, thus allows for prediction of multi-phase/multi-modality (e.g., NC (non-contrast), A (arterial), V (venous), D (delay) contrast phases from dynamic CT scans) and multi-source clinical data with no extra annotation cost. Consistent with the disclosed embodiments, other strategies for finetuning a training module or classification module are also contemplated in the present disclosure. For instance, ADA may be applied to align the distribution of predictions or features between the source and target domains. Self-learning may be applied to generate pseudo-labels, to deduce and correct likely mistakes from the training module and classification module. It is to be noted that other strategies that help create a robust and practical medical image segmentation system are also contemplated in the present disclosure.

The disclosed image segmentation systems, methods, devices, and processes can be applied to segmenting 3D images obtained from any type of imaging modalities, including, but not limited to X-ray, CT, CBCT (cone bear computed tomography), spiral CT, magnetic resonance imaging (MRI), functional MRI (e.g., fMRI, dynamic contrast enhanced (DCE)-MRI and diffusion MM), positron emission tomography (PET), single photon emission computed tomography (SPECT), optical tomography, fluorescence imaging, ultrasound imaging, and radiotherapy portal imaging, etc. Furthermore, the disclosed image segmentation systems, methods, devices, and processes can be used to segment 2D images or other medical images.

Exemplary embodiments are now described with reference to the accompanying drawings. In the figures, the left-most digit(s) of a reference number identifies the figure in which the reference number first appears. Wherever convenient, the same reference numbers are used throughout the drawings to refer to the same or like parts.

FIG. 1 illustrates an exemplary performance of a disclosed image segmentation system, according to some embodiments of the present disclosure.

Dynamic contrast CT is a protocol whereby a patient is imaged under multiple time-points after a contrast agent is injected. The resulting complementary information is critical for characterizing liver lesions. Because accurate segmentation produces important volumetric biomarkers, there is a rich body of work on automatic segmentation, particularly for CT. Despite this, all publicly available data is limited to V-contrast phase (single-channel) CTs. Moreover, when lesions are present, they are typically limited to hepatocellular carcinoma (HCC) or metastasized tumors, lacking representation of intrahepatic cholangio-cellular carcinoma (ICC) or the large bevy of benign lesion types. Additionally, public data may not represent other important scenarios, e.g., the transarterial chemoembolization (TACE) of lesions or splenomegaly, which produce highly distinct imaging patterns. As FIG. 1 illustrates, even impressive leading entries within the public LiTS (liver tumor segmentation benchmark) challenge, can struggle on clinical data, particularly when applied to non-venous contrast phases.

To meet this challenge, powerful but complementary strategies including hetero-modality learning, appearance-based consistency constraints, mask-based ADA, and pseudo-labelling are integrated together in the present disclosure. The result is a semi-supervised model trained on smaller-scale supervised single contrast phase or single modality data and large-scale unsupervised multi-phase/multi-modality data. The disclosed strategy integration avoids serious problems from a naive integration. A key component is co-training, but unlike other existing deep approaches, artificial views are not needed here, instead, each contrast phase or modality is treated as a view. Accordingly, co-training can be adopted with a minimal increase of parameters. Furthermore, since CT studies from clinical datasets may exhibit any combination of phases/modalities, ideally liver segmentation should also be able to accept whatever combination is available, with performance maximizing as more phases/modalities are available. To accomplish this, hetero-modality learning is fused together with co-training, which may be referred to as co-heterogeneous training. Apart from creating a natural hetero-phase/modality model, this has the added advantage of combinatorically exploding the number of views for co-training from 4 to 15, boosting even single-phase/modality performance. To complement these appearance-based semi-supervision strategies, pixel-wise ADA is also applied in the present disclosure, guiding the network to predict masks that follow a proper shape distribution. It is to be noted here, ADA can be applied to co-heterogeneous training with no extra computational cost over adapting a single phase/modality. Moreover, challenging edge cases are also addressed in the present disclosure using a principled pseudo-labelling technique specific to pathological organ segmentation. These different strategies are then combined to produce a powerful segmentation strategy that may be referred to as co-heterogenous and adaptive segmentation (CHASe).

As illustrated in FIG. 1, CHASe-based segmentation strategy out-performs other fully-supervised models on multi-phase/multi-modality data with novel conditions. In the figure, ground truth and predictions are rendered in green and red respectively. Despite performing excellently on labelled source data, other fully-supervised models can struggle on cohorts of multi-phase/multi-modality data with novel conditions, e.g., the patient shown here with splenomegaly and a TACE-treated tumor. CHASe-based segmentation strategy can adopt such models to perform on new data without extra annotation. Hereinafter, more details regarding how CHASe-based strategy can be specifically applied to create a robust and practical segmentation system are provided.

Figure 2:
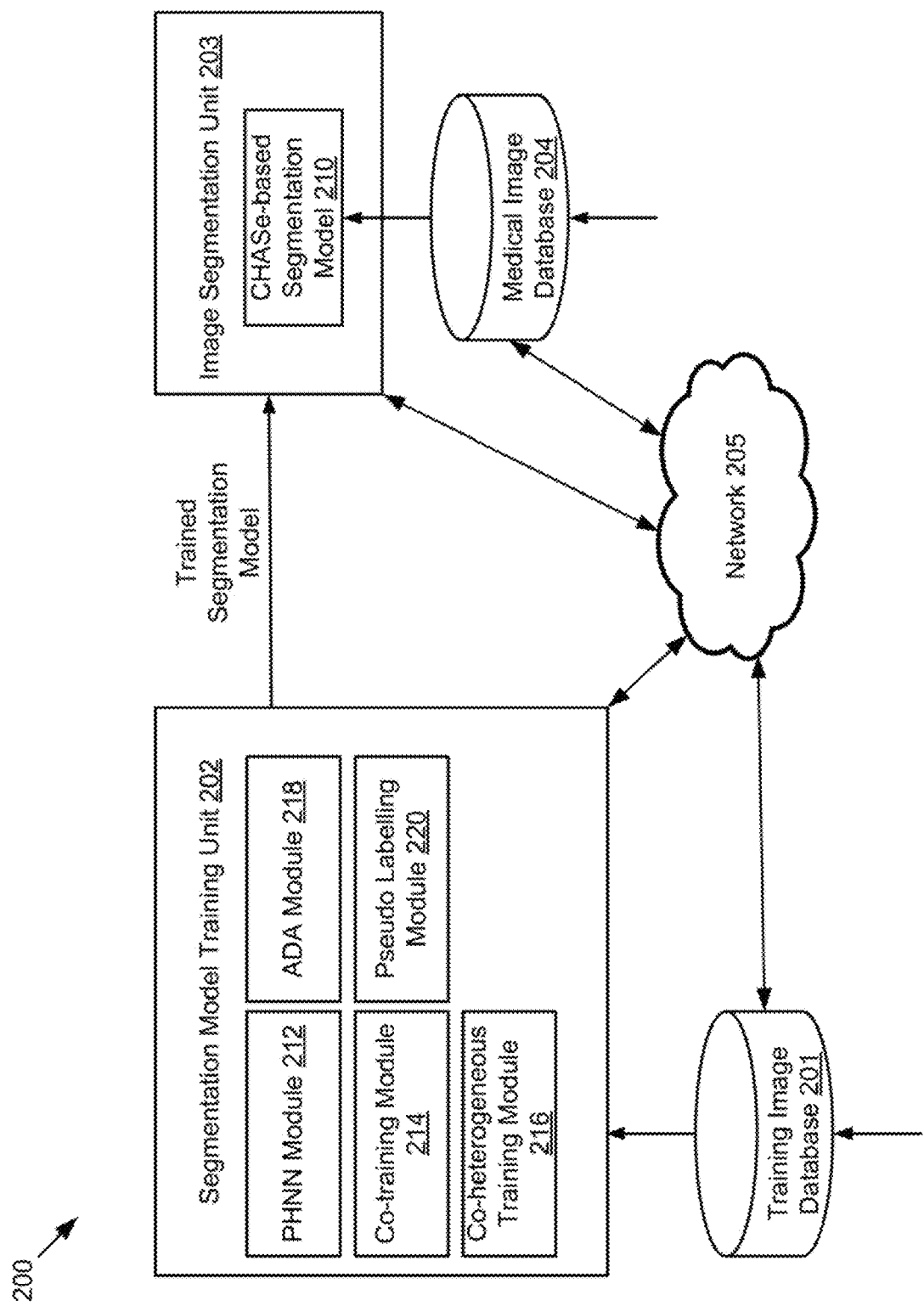
FIG. 2 illustrates an exemplary image segmentation system for segmenting medical images based on learning algorithms, according to some embodiments of the present disclosure.

FIG. 2 illustrates an exemplary image segmentation system 200 for segmenting medical images, according to some embodiments of the present disclosure. Image segmentation system 200 may include a training image database 201, a segmentation model training unit 202, an image segmentation unit 203, a medical image database 204, and a network 205. In some embodiments, image segmentation system 200 may include more or less of the components shown in FIG. 2. For example, when a segmentation model is pre-trained and provided, image segmentation system 200 may only include image segmentation unit 203, medical image database 204, and, optionally, network 205.

In some embodiments, the various components of image segmentation system 200 may locate remotely from each other, and be connected through network 205. In some alternative embodiments, certain components of image segmentation system 200 may be located on the same site or inside one device. For example, training image database 201 may be located on-site with segmentation model training unit 202, or be part of segmentation model training unit 202. As another example, segmentation model training unit 202 and image segmentation unit 203 may be inside the same computer or processing device.

As shown in FIG. 2, segmentation model training unit 202 may communicate with training image database 201 to receive one or more training images. The training images stored in training image database 201 may be obtained from a medical image database, which contains images of previous radiotherapy treatment sessions. In some embodiments, the training images are pre-segmented, curated, or labelled. That is, each image point (pixel or voxel) in the training image is associated with either the background or one of the known anatomical structures contained in the training image. Consistent with the disclosed embodiments, the training images may include MRI images, 3D MRI, 2D streaming MM, 4D volumetric MRI, CT images, CBCT images, Spiral CT images, PET images, functional MRI images (e.g., fMRI, DCE-MRI and diffusion MRI), X-ray images, fluoroscopic images, ultrasound images, radiotherapy portal images, SPECT images, and the like. In some embodiments, a certain number of V-contrast phase CT studies may be collected from different public sources, which may contain a mixture of healthy and pathological livers, with only HCC and metastasis represented. In one example, 235 V-contrast phase CT studies with annotations (i.e., labelled data) are collected from many public sources. This labelled or curated dataset may be referred to as "$D_l$" hereinafter.

In some embodiments, training image database 201 may also include unlabelled medical images. These unlabelled images may be applied to finetune a segmentation model trained through supervised training. For instance, a certain number of multi-phase/multi-modality dynamic CT studies may be directly collected from a medical institute. In one example, 1147 multi-phase/multi-modality dynamic CT studies (4577 volumes in total) are directly collected from the PACS (picture archiving and communication system) of Chang Gung Memorial Hospital (CGMH). The collected dataset may be referred to as "$D_u$" hereinafter. The selection criteria for the unlabelled images may include patients with biopsied or resected liver lesions, with dynamic contrast CTs taken within one month before the procedure. Patients may have ICC, HCC, benign or metastasized tumors, along with co-occurring maladies, such as liver fibrosis, splenomegaly, or TACE-treated tumors. Thus, the dataset may directly reflect the variability found in clinical scenarios.

Segmentation model training unit 202 may use the training images received from training image database 201 to generate a segmentation model using learning algorithms. As shown in FIG. 2, segmentation model training unit 202 may include a PHNN module 212, a co-training module 214, a co-heterogeneous training module 216, an ADA module 218, and a pseudo labelling module 220. Segmentation model training unit 202 may additionally include input and output interfaces (not shown) to communicate with training image database 201 and network 205. Consistent with some embodiments, segmentation model training unit 202 may be implemented with hardware (e.g., as disclosed in FIG. 3) specially programmed by software that performs a segmentation model training process (e.g., as disclosed in FIGS. 4-5).

PHNN module 212 may be configured to develop a PHNN network for image segmentation. The PHNN network has demonstrated leading segmentation performance for many anatomical structures, and thus may be selected as a basis segmentation model for segmenting medical images in the present disclosure. PHNN module 212 may select a PHNN network as the backbone of the segmentation model, and train the selected PHNN network using image data from training image database 201. For instance, the aforementioned curated and labelled dataset $D_l$ may be applied for supervised training of the selected PHNN framework. For more details regarding training the PHNN framework, may refer to the descriptions with respect to FIG. 5.

Since the PHNN framework is trained with curated data $D_l$ at one specific phase/modality, the trained segmentation model may be not readily applicable to dynamic CT data at other phases/modalities. After the supervised training of the PHNN framework, the segmentation model may be further tuned through different strategies as discussed elsewhere herein, to allow the segmentation model to be applied for segmenting clinical images with large variability. Co-training module 214, co-heterogeneous training module 216, ADA module 218, and pseudo labelling module 220 may each apply a respective strategy in finetuning the supervised PHNN framework.

Co-training module 215 may be configured to employ the ubiquitous semi-supervised strategy of enforcing consistency among different phases/modalities. Because dynamic CT consists of the four NC, A, V, and D contrast phases, each of which is matched to same mask, each contrast phase can be regarded as a different view of the same data. This provides for a natural co-training objective of penalizing inconsistencies across mask predictions from different contrast phases/modalities, thereby allowing the segmentation model to be applied to medical images at different contrast phases/modalities. For more details regarding co-training the supervised PHNN framework, may refer to the descriptions with respect to FIG. 5.

Co-heterogeneous training module 216 may be configured to predict masks given any arbitrary combination of input phases/modalities, and thus allow the segmentation model to consume whatever contrast phases/modalities are available and output a unified prediction. It is to be noted that while co-training module 214 may effectively leverage multiple contrast phases/modalities of the unlabelled data, each contrast phase/modality must still be inputted separately into the network, and thus there is no guarantee of a consistent output. Co-heterogeneous training module 216 may address this problem using hetero-modality image segmentation (HeMIS)-style feature fusion. For more details regarding co-heterogeneous training the supervised PHNN framework, may refer to the descriptions with respect to FIG. 5.

ADA module 218 may be configured to train a network to output predictions that follow a prediction distribution learned from labelled data. Segmentation models treated by co-heterogeneous training module 216 may rely on accurate consensus predictions, which may thus struggle to handle significant appearance variations in data (e.g., $D_U$) that are not presented in data (e.g., $D_l$) used for supervised PHNN training. ADA module 218 may address this problem by training a discriminator on a consensus prediction, which adapts the combinatorial number of possible predictions at the same computational cost as performing ADA on only a single prediction, thereby offering an effective and efficient solution. For more details regarding ADA and discriminator training, may refer to the descriptions with respect to FIG. 5.

Pseudo labelling module 220 may be configured to produce effective, domain specific pseudo-labelling, to address edge cases that are not able to be addressed by other modules 212, 214, 216, and 218 in segmentation model training unit 202. For more details regarding pseudo labelling module 220 including how it is used for finetuning the segmentation model, may refer to the descriptions with respect to FIG. 5.

It is to be noted that while five modules 212, 214, 216, 218, and 220 are illustrated in FIG. 2, the disclosed segmentation module training unit 202 is not limited to these modules. Other modules or strategies that help create a robust and practical medical segmentation system are also contemplated. After training by segmentation model training unit 202, the developed segmentation model may be deployed into an image segmentation unit 203 for image segmentation.

Image segmentation unit 203 may receive the trained CHASe-based segmentation model 210 from segmentation model training unit 202. As shown in FIG. 2, image segmentation unit 203 may include trained CHASe-based segmentation model 210. Image segmentation unit 203 may additionally include input and output interfaces (not shown) to communicate with medical image database 204 and network 205. Consistent with some embodiments, image segmentation unit 203 may be implemented with hardware (e.g., as disclosed in FIG. 3) specially programmed by software that performs an image segmentation process.

Image segmentation unit 203 may communicate with medical image database 204 to receive one or more medical images. The medical images stored in medical image database 204 may be obtained from a medical image database, which contains images of radiotherapy treatment sessions. These medical images are typically not segmented yet. Consistent with the disclosed embodiments, the medical images may be acquired using various imaging modalities, include MRI, functional MRI, CT, CBCT, Spiral CT, PET, SPECT, X-ray, fluoroscopic imaging, ultrasound, and radiotherapy portal imaging, etc. In some embodiments, medical image database 204 may be an integrated part of image segmentation unit 203, or located on the same site of image segmentation unit 203, such as in a radiotherapy treatment room. For specific detail regarding the performance of CHASe-based segmentation model 210, may refer to descriptions with respect to FIGS. 8-10.

Network 205 may provide connections between any of the above-described components in image segmentation system 200. For example, network 205 may be a local area network (LAN), a wireless network, a cloud computing environment (e.g., software as a service, platform as a service, infrastructure as a service), a client-server, a wide area network (WAN), and the like.

Figure 3:
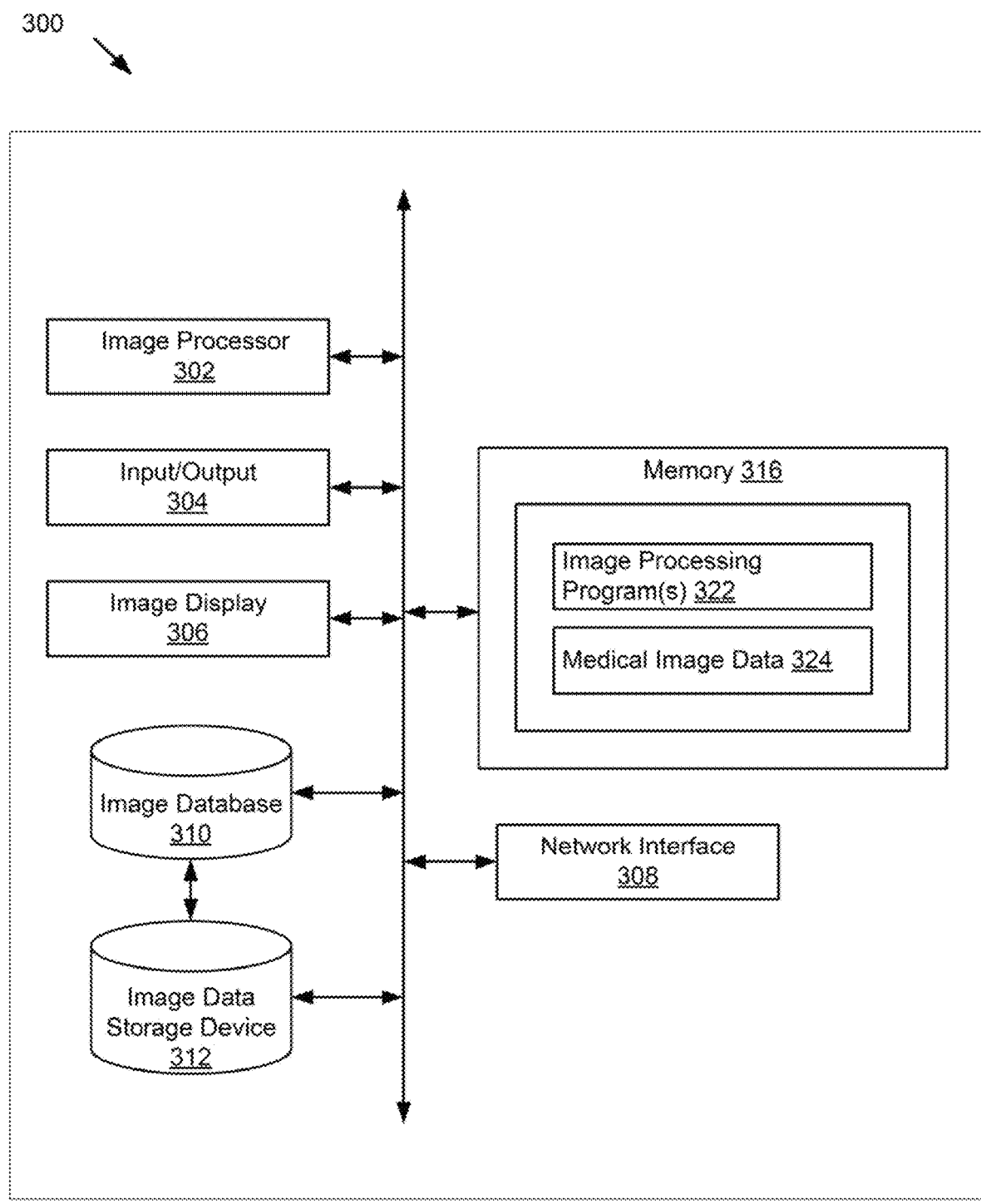
FIG. 3 illustrates an exemplary medical image processing device, according to some embodiments of the present disclosure.

Referring now to FIG. 3, an exemplary medical image processing device 300 is provided, according to some embodiments of the present disclosure. Medical image processing device 300 may be an embodiment of segmentation model training unit 202, or image segmentation unit 203, or the combination of the two. As would be appreciated by those skilled in the art, in some embodiments, medical image processing device 300 may be a special-purpose computer, or a general-purpose computer. For example, medical image processing device 300 may be a computer custom built for hospitals to handle image acquisition and image processing tasks.

As shown in FIG. 3, medical image processing device 300 may include an image processor 302, an input/output 304, an image display 306, a network interface 308, an image database 310, an image data storage device 312, and a memory 316.

Image processor 302 may be a processing device, including one or more general-purpose processing devices such as a microprocessor, central processing unit (CPU), graphics processing unit (GPU), or the like. More particularly, image processor 302 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets. Image processor 302 may also be one or more special-purpose processing devices such as an application specific integrated circuit (ASIC), a field programmable gate array (FPGA), a digital signal processor (DSP), a System on a Chip (SoC), or the like.

Image processor 302 may be communicatively coupled to memory 316 and configured to execute the computer executable instructions or programs stored thereon. Memory 316 may include a read-only memory (ROM), a flash memory, a random access memory (RAM), a static memory, etc. In some embodiments, memory 316 may store computer executable instructions, such as one or more image processing programs 322, as well as data used or generated while executing the computer programs 322, such as medical image data. Image processor 302 may execute image processing programs 322 to implement functionalities of segmentation model training unit 202 and/or image segmentation unit 203. Image processor 302 may also send/receive medical image data 324 from memory 316. For example, image processor 302 may receive training image data or medical image data stored in memory 316. Image processor 302 may also generate intermediate data such as landmark features, and send them to memory 316.

Medical image processing device 300 may optionally include an image database 310, which includes one or both of training image database 201 and medical image database 204. One skilled in the art would appreciate that image database 310 may include a plurality of devices located either in a central or distributed manner. Image processor 302 may communicate with mage database 310 to read images into memory 316 or store segmented images from memory 316 to image database 310.

Image data storage device 312 may be an additional storage available to store data associated with image processing tasks performed by image processor 302. In some embodiments, image data storage device 312 may include a machine-readable storage medium. While the machine-readable storage medium in an embodiment may be a single medium, the term "machine-readable storage medium" should be taken to include a single medium or multiple media (e.g., a centralized or distributed database, and/or associated caches and servers) that store the one or more sets of computer executable instructions or data. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical and magnetic media.

Input/output 304 may be configured to allow data to be received and/or transmitted by medical image processing device 300. Input/output 304 may include one or more digital and/or analog communication devices that allow medical image processing device 300 to communicate with user or other machines and devices. For example, input/output 304 may include a keyboard and a mouse for a user to provide input.

Image display 306 may be any display device that suitable for displaying the medical images. For example, image display 306 may be an LCD, CRT, or LED display.

Network interface 308 may include a network adaptor, a cable connector, a serial connector, a USB connector, a parallel connector, a high-speed data transmission adaptor such as fiber, USB 3.0, thunderbolt, and the like, a wireless network adaptor such as a WiFi adaptor, a telecommunication (3G, 4G/LTE and the like) adaptor, and the like. Medical image processing device 300 may be connected to network 205 through network interface 308.

Image processing programs 322 in memory 316 may include any programs that facilitate image processing. When implemented by image processor 302, image processing programs 322 may allow medical images to be processed in medical image processing device 300. For instance, image processing programs 322 may include a CHASe-based segmentation model 210 for segmenting medical images with large variability. In some embodiments, image processing programs 322 may also include programs for training a CHASe-based segmentation model. For instance, image processing programs 322 may include PHNN module 212, co-training module 214, co-heterogeneous training module 216, ADA module 218, and pseudo labelling module 220 that together implement CHASe-based strategies for developing robust and practical segmentation models.

Figure 4:
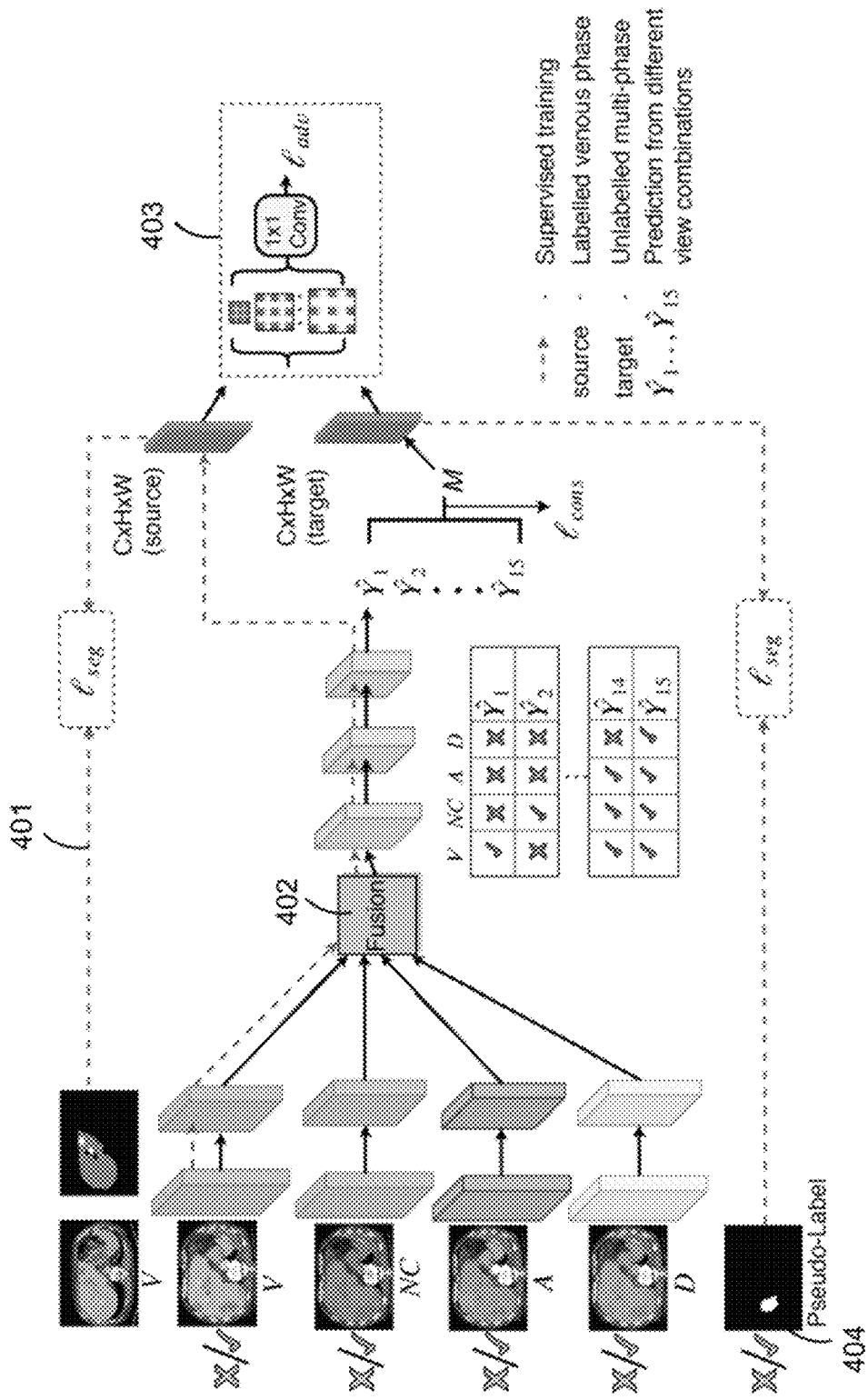
FIG. 4 illustrates an overview of training a CHASe-based segmentation model, according to some embodiments of the present disclosure.

FIG. 4 illustrates an overview of the CHASe-based strategy, according to some embodiments of the present disclosure. The CHASe-based strategy starts by training a standard fully supervised segmentation model using the labelled data. Next, under CHASe, the model is finetuned using consistency and ADA losses:

$$L = L_{seg} + L_{cons} + \lambda_{adv} * L_{adv} \quad (1)$$

where L, $L_{seg}$, $L_{cons}$, $L_{adv}$ are the overall, supervised, co-heterogenous, and ADA losses, respectively. As illustrated in FIG. 4, a supervised loss may be produced at supervised training process 401 using curated and labelled data and a supervised training process 404 using pseudo labelled data, a co-heterogenous loss may be produced at a co-heterogeneous training process 402, and an ADA loss may be produced at an ADA process 403. When these losses are considered together, a more robust segmentation model may be then developed. To set up adversarial optimization, a discriminator loss, $L_d$, may also be deployed in competition with formulation (1). For specific detail regarding the above losses, may refer to the descriptions in FIG. 5.

Figure 5:
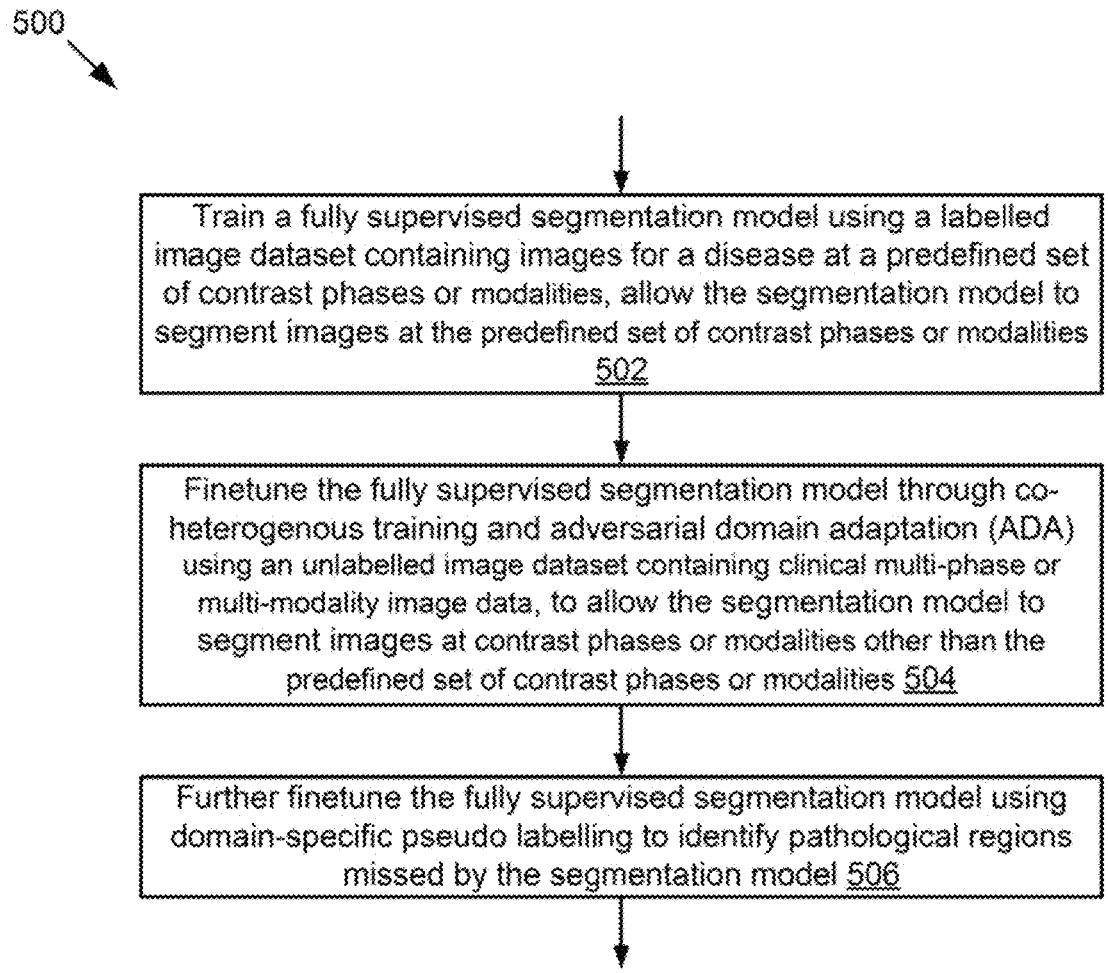
FIG. 5 is a flowchart illustrating an exemplary segmentation model training process, according to some embodiments of the present disclosure.

FIG. 5 is a flowchart illustrating an exemplary imaging process method that includes a segmentation model training process 500 for training a segmentation model for segmenting multi-phase/multi-modality and multi-source clinical three-dimensional image data, according to some embodiments of the present disclosure. In some embodiments, segmentation model training process 500 may be performed by segmentation model training unit 202.

Process 500 may start, in Step 502, by training a fully supervised segmentation model using a labelled image dataset containing images for a disease at a predefined set of contrast phases or modalities. To achieve this, segmentation model training unit 202 may receive a training image dataset for a region of interest from training image database 201. For example, the training image dataset may show the pelvic area, the head area, the cardiac area, the liver area, or another anatomical area of a patient. In some embodiments, the training image dataset may be of a same or similar region of interest as the medical image to be segmented. For instance, the training image dataset may include CT scans and masks from a public data source. In one example, to allow a fully supervised training of the segmentation model, the obtained dataset may be a curated and labelled dataset of CTs and scans for liver, such as the aforementioned $D_l$.

For ease of interpretation, the above-described dataset obtained by segmentation model training unit 202 may be denoted as $Y_i(k) \in \{0,1,2\}$ with $X_i$ denoting the set of available contrast phases or modalities and $Y_i(k) \in \{0,1,2\}$ indicating background, liver, and lesion for all pixel/voxel indices k. In some embodiments, without loss of generality, the CTs may be all V-contrast phase, i.e., $X_i = V_i \forall X_i \in D_l$.

In some embodiments, segmentation model training unit 202 may reply on an FCN, $f(\cdot)$ as the backbone of to-be-trained segmentation model. For instance, a U-Net or V-net style encoder/decoder may be used as the backbone. In some embodiment, a PHNN framework may be applied here. The PHNN framework has demonstrated leading segmentation performance for many anatomical structures, sometimes even outperforming U-Net. More importantly, PHNN has roughly half the parameters and activation maps of an equivalent encoder/decoder. As discussed, since the to-be-trained segmentation model will include additional components for semi-supervised learning, this light-weightiness is a crucial factor.

FIG. 5 depicts an exemplary structure of PHNN. In some embodiments, PHNN relies on deep supervision in lieu of a decoder and assumes the FCN can be broken into stages based on pooling layers. With no loss of generality, there may exist five FCN stages, which matches popular FCN configurations. PHNN produces a sequence of logits, $a^{(m)}$, using 1×1 convolutions and upsamplings operating on the terminal backbone activations of each stage. Sharing similarities to residual connections, predictions may be generated for each stage using a progressive scheme that adds to the previous stage's activations:

$$\hat{Y}^{(1)} = \sigma(\alpha^{(1)}) \quad (2)$$

$$\hat{Y}^{(m)} = \sigma(\alpha^{(m)} + \alpha^{(m-1)}) \forall m > 1 \quad (3)$$

where $\sigma(\cdot)$ denotes the softmax operator and $\hat{Y}^{(\cdot)}$ represents the predictions, with the final stage's predictions acting as the actual segmentation output, $\hat{Y}$. Being deeply supervised, PHNN may optimize a segmentation loss at each stage:

$$l_{seg}(f(V), Y) = \sum_{j=0}^{5} \frac{m}{5} l_{ce}(\hat{Y}^m, Y) \quad (4)$$

where $l_{ce}(\cdot, \cdot)$ is a cross-entropy loss weighted via prevalence. In some embodiments, later stages are weighted here.

From the above, prior to any semi-supervised learning, the PHNN framework may be first trained using the predefined set of contrast phases and modalities of data set. For instance, segmentation model training unit 202 may train the PHNN framework using $D_l$ as follow:

$$L_{seg} = \frac{1}{N_l} \sum_{V,Y \in D_l} l_{seg}(f(V), Y) \quad (5)$$

After fully supervised training by the dataset of the predefined set of contrast phases or modalities, the PHNN framework may subject to further finetuning processes to allow the trained PHNN framework to segment contrast phases or modalities other than the predefined set of contrast phases and modalities, as described in detail below.

In Step 504, the fully supervised segmentation model may be finetuned through co-heterogenous training and ADA using an unlabelled image dataset containing clinical multi-phase or multi-modality image data.

Figure 6:
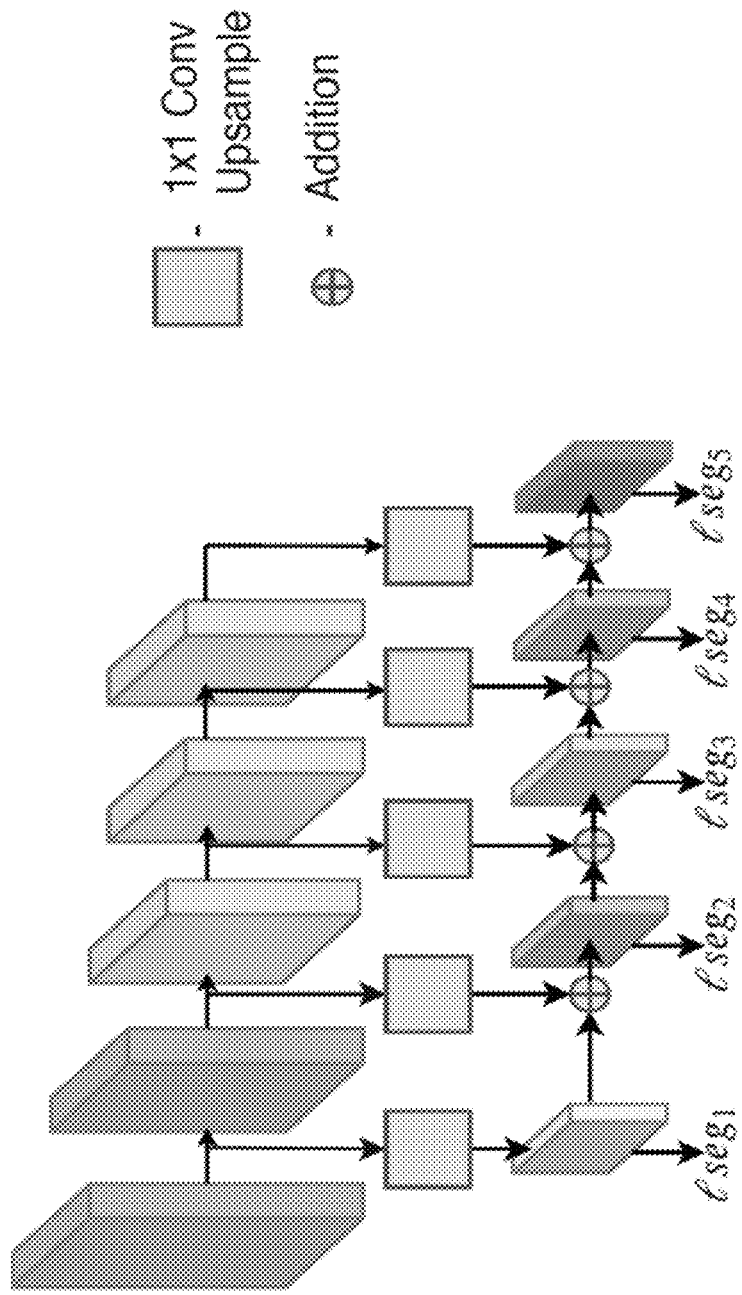
FIG. 6 illustrates an exemplary deeply-supervised progressive holistically nested network framework, according to some embodiments of the present disclosure.

In some embodiments, since dynamic CT includes four NC, A, V, and D contrast phases, each of which is matched to a same mask, Y, and each contrast phase may be regarded as a different view of the same data. This then provides for a natural co-training objective of penalizing inconsistencies across mask predictions from different contrast phases. To achieve this, predictions for each contrast phase may be created. As illustrated in FIG. 6, this may be accomplished using phase-specific FCN stages, i.e., the first two low-level stages, and then using a shared set of weights for the later semantic stages. Because convolutional weights are greater in number in later stages, this allows for a highly efficient multi-phase setup. All layer weights may be initialized using the corresponding fully supervised V-contrast phase weights as previously described, including the phase-specific layers. It is to be noted that activations across contrast phases remain distinct. Despite the distinct activations, for convenience, $\hat{y}=f(X)$ may still be used to denote the generation of all phase predictions for one data instance. When all four phases are available in X, then $\hat{y}$ corresponds to $\{\hat{Y}^{NC}, \hat{Y}^A, \hat{Y}^V, \hat{Y}^D\}$.

In some embodiments, to penalize inconsistencies, the Jensen-Shannon divergence (JSD) may be applied here. In some embodiments, the JSD may be devised by first devising a consensus prediction:

$$M = \frac{1}{|\hat{y}|} \sum_{\hat{Y} \in \hat{y}} \hat{Y} \quad (6)$$

Accordingly, the JSD may be expressed as the divergence between the consensus prediction and each prediction:

$$l_{cons}(f(X)) = \frac{1}{|\hat{y}|} = \sum_{\hat{Y} \in \hat{y}} \sum_{k \in \Omega} KL(\hat{Y}(k) \| M(k)) \quad (7)$$

$$L_{cons} = \frac{1}{N_u} \sum_{X \in D_u} l_{cons}(f(X)) \quad (8)$$

where $\Omega$ denotes the spatial domain and $KL(\cdot\|\cdot)$ corresponds to the Kullback-Leibler divergence taken across the prediction classes. Cast in this way, co-training may be regarded as a form of self-learning, where the pseudo-labels correspond to the consensus prediction in formulation (6). When using the deeply supervised PHNN, only the JSD across the final prediction is calculated.

It is to be noted that while minimizing the loss in formulation (8) can effectively leverage multiple contrast phases of the unlabelled data, it is not completely satisfactory. Namely, each contrast phase must still be inputted separately into the network, and there is no guarantee of a consistent output. Despite only having single-phase labelled data, ideally, the network should be adapted for multi-phase/multi-modality operation on $D_u$, meaning it should be able to consume whatever contrast phases are available and output a unified prediction that is stronger as more contrast phases are available.

To achieve the above, a HeMIS-style feature fusion may be applied here, which can predict masks given any arbitrary combination of input phases, or contrast phases or modalities. Specifically, a set of phase/modality-specific layers may produce a set of phase/modality-specific activations, A, cardinality of which may depend on the number of inputs. The activations may be then fused together using first- and second-order statistics, which are flexible enough to handle any number of inputs:

$$\alpha_{fuse} = \text{concat}(\mu(A), \text{var}(A)) \quad (9)$$

where $\alpha_{fuse}$ denotes the fused feature, and the mean and variance may be taken across the available phases/modalities. When only one phase/modality is available, the variance features may be set to 0. To fuse intermediate predictions, an additional necessity for deeply supervised networks, their mean may be taken for the purpose.

In some embodiments, for choosing a fusion point, the choice of co-training setup, with its phase/modality-specific layers, may already offer a natural fusion location. Accordingly, hetero-phase learning with co-training can be readily combined, re-defining a "view" to mean any possible combination of the four contrast phases. This may have the added benefit of combinatorically exploding the number of co-training views. More formally, $X^* = P(X) \setminus \{\phi\}$ may be used to denote all possible contrast-phase/modality combinations, where $P(\cdot)$ is the powerset operator. The corresponding predictions may be denoted as $\hat{y}^*$. When a data instance has all four phases, then the cardinality of $X^*$ and $\hat{y}^*$ is 15, which is a drastic increase in views.

With hetero-modality fusion in place, the consensus prediction and co-training loss of formulations (6) and (7), respectively, may be supplanted by ones that use $\hat{y}^*$:

$$M = \frac{1}{|\hat{y}*|} \sum_{\hat{Y} \in \hat{y}*} \hat{Y} \quad (10)$$

$$l_{cons}(f(X)) = \frac{1}{|\hat{y}*|} \sum_{\hat{Y} \in \hat{y}*} \sum_{k \in \Omega} KL(\hat{Y}(k) \| M(k)) \quad (11)$$

When only single-phase/modality combinations are used, formulations (10) and (11) may reduce to standard co-training.

It is to be noted that while co-heterogeneous training is highly effective, it relies on accurate consensus predictions, which may struggle to handle significant appearance variations in $D_u$ that are not represented in $D_l$. ADA offers an alternative and complementary approach, provided it is used to train a network to output predictions that follow a prediction distribution learned from labelled data. Since liver shapes between $D_u$ and $D_l$ are expected to follow similar distributions, ADA provides an effective learning strategy that is not as confounded by differences in appearance. Accordingly, a discriminator may be trained to classify whether a softmax output originates from a labelled- or unlabelled-dataset prediction. However, since there are a combinatorial number (15) of possible input phase/modality combinations, i.e., $\hat{X}^*$, naively domain-adapting all corresponding predictions is prohibitively expensive.

In some embodiments, the formulations of (7) and (11) offer an effective and efficient solution. Namely, the discriminator may be trained on the consensus prediction, M, as shown in FIG. 4. This adapts the combinatorial number of possible predictions at the same computational cost as performing ADA on only a single prediction.

Specifically, let d(•) be defined as an FCN discriminator, then the discriminator loss can be expressed as $$L_d = \frac{1}{N_l} \sum_{D_l} l_{ce}\left(d\left(\hat{Y}^V\right), 1\right) + \frac{1}{N_u} \sum_{D_u} l_{ce}(d(M, 0)) \quad (12)$$

where $l_{ce}$ represents a pixel-wise cross-entropy loss. The opposing labels may push the discriminator to differentiate semi-supervised consensus predictions from fully supervised variants. Unlike natural image ADA, it is not intended to naively train the discriminator on all output classes, as it is not reasonable to expect similar distributions of liver lesion shapes across datasets. Instead, the discriminator on the liver region may be trained, i.e., the union of healthy liver and lesion tissue predictions. In fact, when minimizing formulation (12), only the discriminator weights are optimized. The segmentation network can now be tasked with fooling the discriminator, through the addition of an adversarial loss:

$$L_{adv} = \frac{1}{N_u} \sum_{D_u} l_{ce}(d(M, 1)) \quad (13)$$

where the ground-truth labels for $l_{ce}$ have been flipped from formulation (12). It is to be noted that single-level ADA is used here, as the multi-level variant may fail to offer significant enough improvements to offset the added complexity. When minimizing formulations (13), or (1) for that matter, the discriminator weights may be frozen. At this point, $\lambda_{adv}$ may be empirically set to 0.001.

It is to be noted while the above finetuned segmentation model can robustly segment challenging multi-phase/multi-modality unlabelled data with an effective integration of co-heterogeneous training and ADA, some application scenarios still present challenging edge cases, e.g., lesions treated with TACE. To manage these edge cases, a simple, but effective, domain-specific pseudo-labelling may be further applied here to continue finetuning the already finetuned segmentation model.

Figure 7:
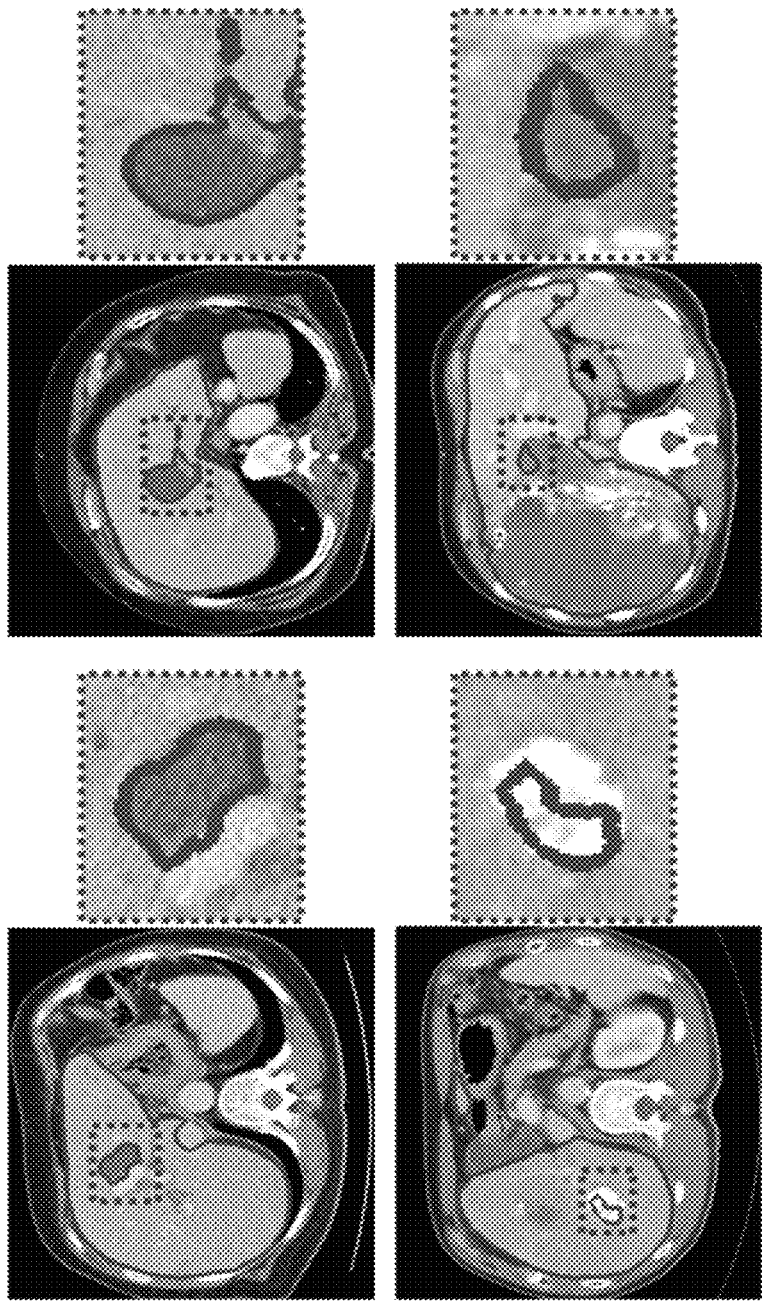
FIG. 7 illustrates exemplary hole-based pseudo modelling, according to some embodiments of the present disclosure.

In Step 506, segmentation model training unit 202 may further finetune the already tuned segmentation model using domain-specific pseudo labelling. Specifically, after convergence of formulation (1), predictions may be generated on $D_u$ using all available contrast phases or modalities and any resulting 3D holes in the liver region greater than 100 voxels may be then extracted. For instance, bottom left of FIG. 7 shows a TACE-treated lesion, which is not seen in public datasets, which may be extracted. Since there should never be 3D holes, these are mistakes. Under the assumption that healthy tissue in both datasets should be equally represented, these holes may be treated as missing "lesion" predictions. Accordingly, a pseudo-label, $Y_h$ may be created, to indicates lesion at the hole, with all other regions being ignored. This may then produce a new "holes" dataset, $D_h = \{X, Y_h\}_{i=1}^{N_h}$, using image sets extracted from $D_u$. The model may be then finetuned using formulation (1), but by replacing the segmentation loss of formulation (5) by:

$$L_{seg} = \frac{1}{N_l} \sum_{V,Y \in D_l} l_{seg}(f(V), Y) + \frac{\lambda_h}{N_h} \sum_{X,Y_h \in D_h} \sum_{X \in X_*} l_{seg}(f(X), Y_h) \quad (14)$$

where $\lambda_h$ may be empirically set to 0.01 for all experiments. In some embodiments, results are not sensitive to this empirically set value.

It is to be noted that while the hole-based pseudo-labels do not capture all errors, they only have to capture enough of missing appearances to guide CHASe's training to better handle recalcitrant edge cases (e.g., lesions treated with TACE).

It is also to be noted that hole-based pseudo-labeling is not just applied for lesions as discussed above, but can also be applied to any anomalous or pathological region missed by the fully supervised and/or finetuned segmentation model.

After integration of the powerful but complementary strategies as described in Steps 502-506 as illustrated in FIG. 5, a semi-supervised CHASe-based segmentation model trained on smaller-scale supervised V-contrast phase data and large scale unsupervised multi-phase/multi-modality data is obtained. This semi-supervised segmentation model may be then applied to different unlabelled datasets for image segmentation.

TABLE 1

| Models | NC (96) | | A (98) | | V (97) | | D (98) | | All (100) | |
|---|---|---|---|---|---|---|---|---|---|---|
| | DSC | ASSD | DSC | ASSD | DSC | ASSD | DSC | ASSD | DSC | ASSD |
| HDenseUNet [25] | 85.2 | 3.25 | 90.1 | 2.19 | 90.7 | 2.61 | 85.2 | 2.91 | 89.9 | 2.59 |
| Baseline [14] | 84.6 | 2.97 | 90.3 | 1.23 | 90.7 | 1.18 | 86.7 | 2.12 | 91.4 | 1.21 |
| Baseline w pseudo | 89.4 | 1.97 | 90.5 | 1.34 | 90.9 | 1.29 | 90.6 | 2.03 | 91.9 | 1.27 |
| Baseline w ADA [40] | 90.9 | 1.34 | 91.9 | 1.13 | 91.5 | 1.14 | 90.9 | 1.65 | 92.6 | 1.03 |
| Co-training [31] | 92.8 | 0.95 | 93.4 | 0.84 | 93.4 | 0.83 | 92.4 | 0.99 | 94.0 | 0.92 |
| Co-hetero | 93.4 | 0.81 | 93.7 | 0.77 | 94.5 | 0.79 | 93.6 | 0.86 | 94.7 | 0.89 |
| Co-hetero w ADA | 93.8 | 0.81 | 93.9 | 0.79 | 94.8 | 0.66 | 93.9 | 0.81 | 95.0 | 0.68 |
| CHASe | 94.0 | 0.79 | 94.2 | 0.74 | 94.9 | 0.66 | 94.1 | 0.80 | 95.4 | 0.63 |

Figure 8:
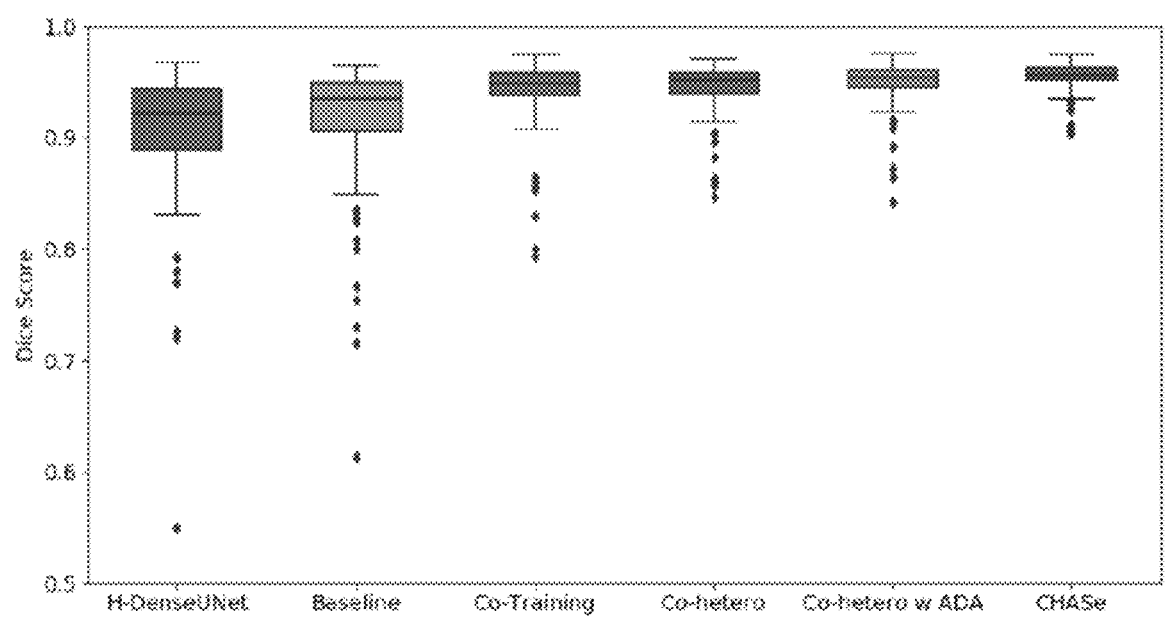
FIG. 8 illustrates exemplary quantitative segmentation results, according to some embodiments of the present disclosure.

Table 1 and FIG. 8 illustrates exemplary quantitative segmentation results according to some embodiments of the present disclosure. As Table 1 indicates, despite being only a single 2D network, the PHNN baseline is strong, comparing similarly to the cascaded 2D/3D H-DenseUNet. However, both H-DenseUNet and PHNN baseline still struggle to perform well on the dataset $D_u$, particularly on non-V-contrast phases, indicating that training on public V-contrast phase data alone is not sufficient. In contrast, through its principled semi-supervised approach, CHASe-based segmentation model (may be simply referred to as "CHASe" throughout the disclosure) is able to dramatically increase performance, producing boosts of 9.4%, 3.9%, 4.2%, 7.4%, and 4.0% in mean DSCs (Dice-Sorensen coefficient) for inputs of NC, A, V, D, and all phases, respectively. As can also be seen, all components contribute to these improvements, indicating the importance of each strategy to the final result. Compared to established baselines of co-training and ADA, CHASe garners marked improvements. In addition, CHASe performs more strongly as more contrast phases or modalities are available, something the baseline models are not always able to do. Results across all 15 possible combinations also demonstrate this trend.

While these mean-valued metrics are persuasive, even more compelling results can be found box and whisker plots in FIG. 8. As can be seen, each component is not only able to reduce variability, but more importantly significantly improve worst-case results. These same trends can be seen across all possible phase/modality combinations. Compared to improvements in mean DSCs, these worst-case reductions, with commensurate boosts in reliability, can often be more impactful for clinical applications.

Table 1 demonstrates that fully supervised baselines may struggle when faced with new data. The disclosed CHASe-based approach, however, achieves comparable, or better, DSCs on a large number of pathological multi-phase/multi-modality test studies. Therefore, CHASe is able to provide tangible improvements in consistency and reliability, robustly predicting even when presented with image features not seen in V-contrast phase dataset.

Figure 9:
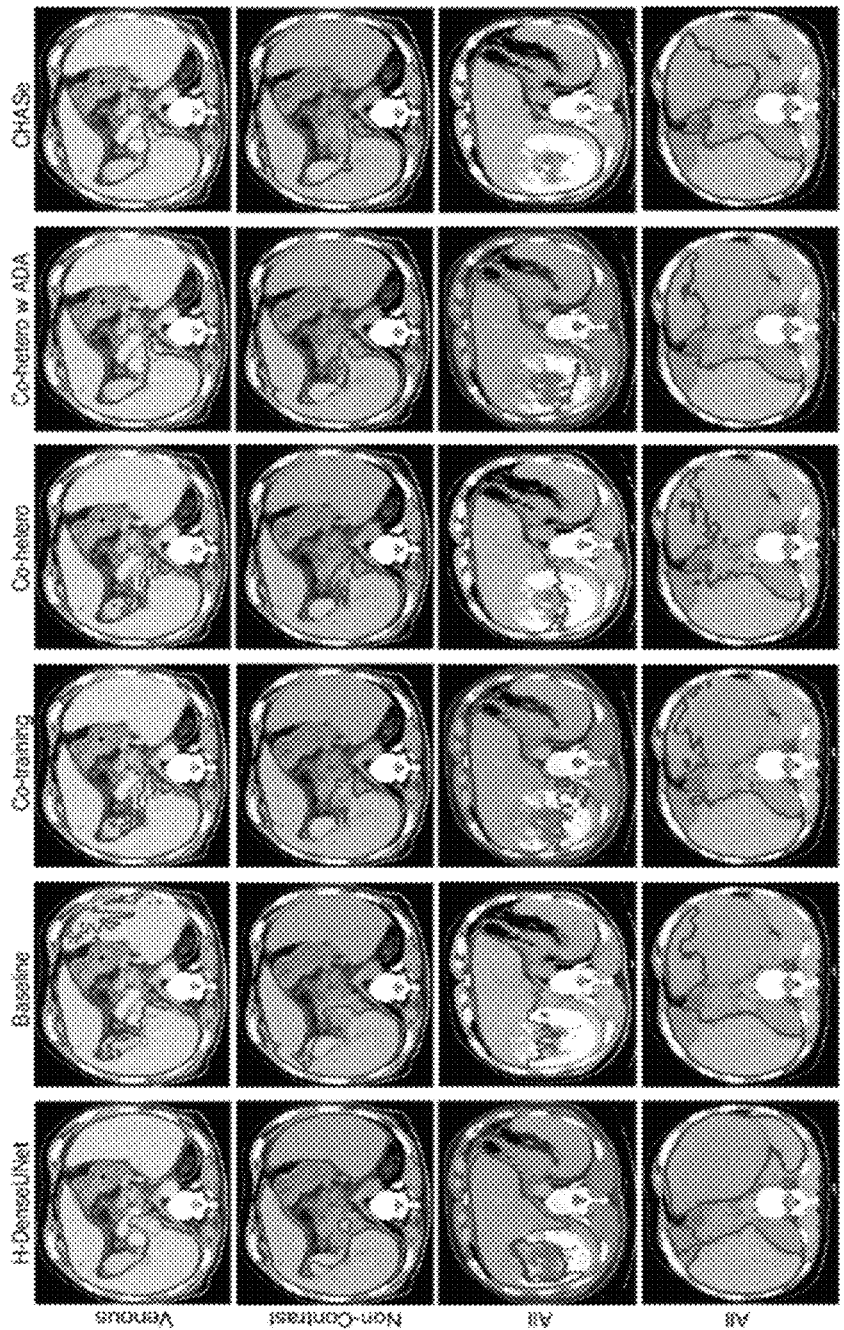
FIG. 9 illustrates exemplary qualitative segmentation results, according to some embodiments of the present disclosure.

FIG. 9 illustrates exemplary qualitative results according to some embodiments. As the first two rows demonstrate, H-DenseUNet and the baseline can perform inconsistently across contrast phases, with both being confused by the splenomegaly (overly large spleen) of the sample patient. The CHASe components (i.e., CHASe-based segmentation model and the corresponding models produced during the development of the CHASe-based segmentation model) are able to correct these issues. The third row depicts an example of a TACE-treated lesion, not seen in the public dataset and demonstrates how CHASe's components can progressively correct the under-segmentation. Finally, the last row depicts the worst-case performance of CHASe. Despite this unfavorable selection, CHASe is still able to predict better masks than the alternatives. Green and red curves depict the ground truth and segmentation predictions, respectively.

Figure 10:
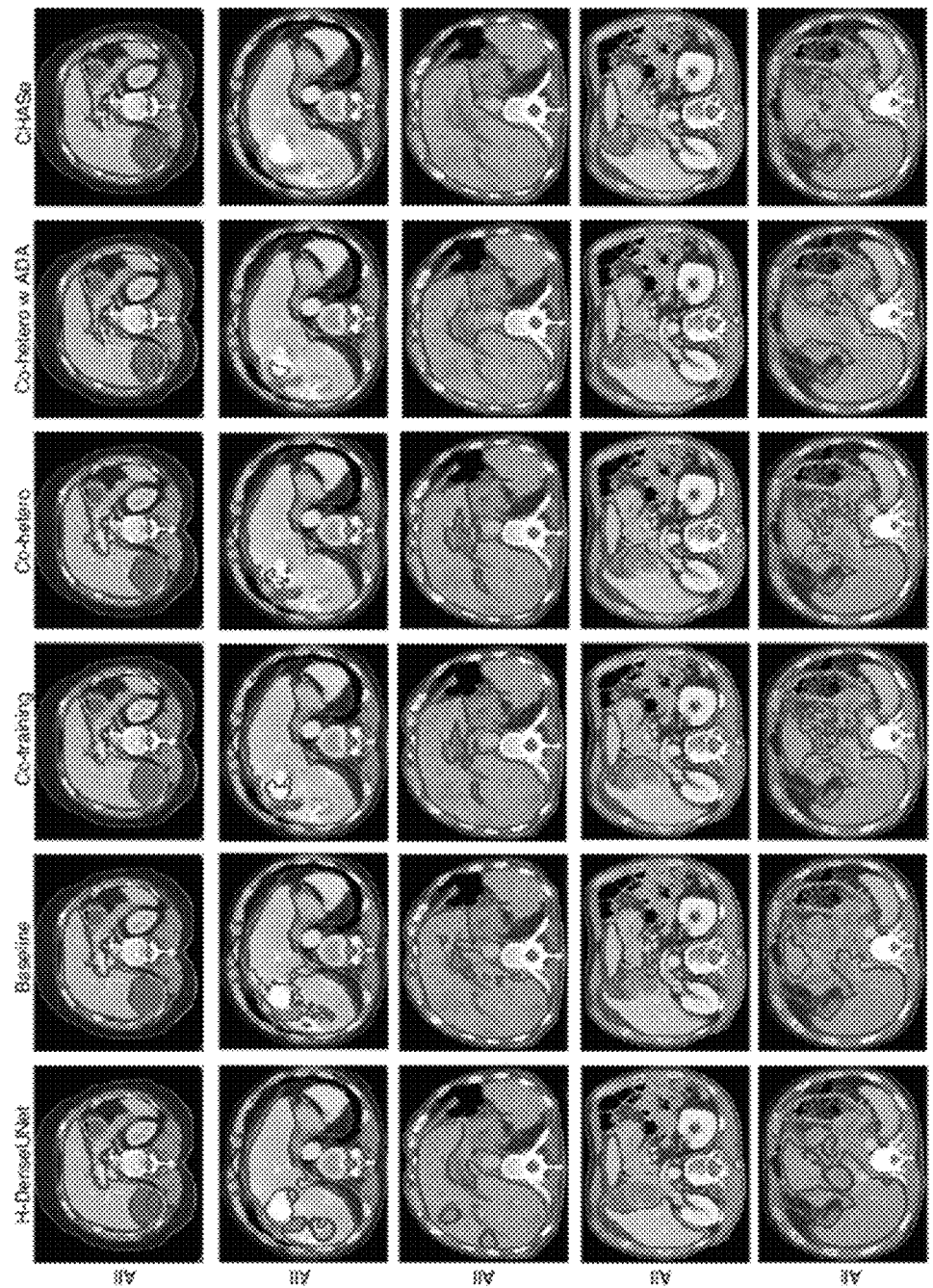
FIG. 10 illustrates another set of exemplary qualitative segmentation results, according to some embodiments of the present disclosure.

FIG. 10 illustrates another set of exemplary qualitative results according to some embodiments. Green and red curves depict the ground truth and segmentation predictions, respectively. All predictions executed with all contrast phases are used as input. The first and last rows depict failure cases, where the latter is an extremely challenging case with an extraordinarily large lesion occupying much of the liver space. CHASe still manages to provide superior results compared to the alternatives. The second row demonstrates CHASe's ability to account for TACE-treated lesions, which are not present in public datasets. The fourth row depicts another highly challenging case, where the gallbladder is difficult to distinguish from a lesion. As can be seen, CHASe is the only model able to successfully differentiate these two structures.

From these qualitative and quantitative results, it can be seen that the CHASe-based segmentation model based on the disclosed strategies can reflect clinical conditions well, which leads to drastic performance improvement in medical image segmentation.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present invention also relates to a system for performing the operations herein. This system may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A computer-implemented method for processing clinical three-dimensional image, the method comprising:
    training a fully supervised segmentation model using a labelled image dataset containing images for a disease at a predefined set of contrast phases or modalities, to allow a segmentation model to segment images at the predefined set of contrast phases or modalities;
    finetuning the fully supervised segmentation model through co-heterogenous training and adversarial domain adaptation (ADA) using an unlabelled image dataset containing clinical multi-phase or multi-modality image data, to allow the segmentation model to segment images at contrast phases or modalities other than the predefined set of contrast phases or modalities; and
    further finetuning the fully supervised segmentation model using domain-specific pseudo labelling to identify pathological regions missed by the segmentation model.

2. The method of claim 1, wherein training the fully supervised segmentation model using the labelled image dataset includes:
    receiving a curated and labelled dataset of clinical three-dimensional images and masks;
    selecting a progressive holistically nested network (PHNN) framework; and
    training, through a supervised learning, the PHNN framework using the curated and labelled dataset of clinical three-dimensional images and masks, to obtain the fully supervised segmentation model.

3. The method of claim 1, wherein the co-heterogenous training includes fusing hetero-modal learning with co-training to form a multi-modal learning for performing appearance-based learning from the unlabelled image dataset.

4. The method of claim 1, wherein the ADA includes training the fully supervised segmentation model to output predictions that follow a prediction distribution learned from the labelled image dataset by the segmentation model.

5. The method of claim 1, wherein finetuning the fully supervised segmentation model through the co-heterogenous training and the ADA using the unlabelled image dataset includes:
    finetuning the segmentation model using a formulation: $L = L_{seg} + L_{cons} + \lambda_{adv} * L_{adv}$, wherein L, $L_{seg}$, $L_{cons}$, $L_{adv}$ are an overall, supervised, co-heterogenous, and ADA losses, respectively.

6. The method of claim 5, wherein finetuning the fully supervised segmentation model using the domain-specific pseudo labelling includes:
    producing predictions on the unlabelled image dataset after the fully supervised segmentation model is finetuned through the co-heterogenous training and the ADA;
    extracting 3D holes in tissue regions greater than 100 voxels;
    creating a pseudo label for indicating a pathological region at each extracted hole, to obtain a "holes" dataset; and
    finetuning the fully supervised segmentation model by replacing $L_{seg}$ with a segmentation loss obtained according to the "holes" dataset.

7. The method of claim 1, wherein the labelled image dataset includes a dataset with a number of curated and labelled V-phase liver images including CT scans and masks.

8. The method of claim 1, wherein the unlabelled image dataset includes a number of unlabelled multi-phase or multi-modality CTs from an uncurated clinical source.

9. A computer program product comprising a non-transitory computer readable storage medium and program instructions stored therein, the program instructions being configured to be executable by a computer to cause the computer to perform operations comprising:
    training a fully supervised segmentation model using a labelled image dataset containing images for a disease at a predefined set of contrast phases or modalities, to allow a segmentation model to segment images at the predefined set of contrast phases or modalities;
    finetuning the fully supervised segmentation model through co-heterogenous training and ADA using an unlabelled image dataset containing clinical multi-phase or multi-modality image data, to allow the segmentation model to segment images at contrast phases or modalities other than the predefined set of contrast phases or modalities; and
    further finetuning the fully supervised segmentation model using domain-specific pseudo labelling to identify pathological regions missed by the segmentation model.

10. The product of claim 9, wherein training the fully supervised segmentation model using the labelled image dataset includes:
    receiving a curated and labelled dataset of clinical three-dimensional images and masks;
    selecting a PHNN framework; and
    training, through a supervised learning, the PHNN framework using the curated and labelled dataset of clinical three-dimensional images and masks, to obtain the fully supervised segmentation model.

11. The product of claim 9, wherein the co-heterogenous training includes fusing hetero-modal learning with co-training to form a multi-modal learning for performing appearance-based learning from the unlabelled image dataset.

12. The product of claim 9, wherein the ADA includes training the fully supervised segmentation model to output predictions that follow a prediction distribution learned from the labelled image dataset by the segmentation model.

13. The product of claim 9, wherein finetuning the fully supervised segmentation model through the co-heterogenous training and the ADA using the unlabelled image dataset includes:

finetuning the segmentation model using a formulation: $L=L_{seg}+L_{cons}+\lambda_{adv}*L_{adv}$, wherein $L$, $L_{seg}$, $L_{cons}$, $L_{adv}$ are an overall, supervised, co-heterogenous, and ADA losses, respectively.

14. The product of claim 13, wherein finetuning the fully supervised segmentation model using the domain-specific pseudo labelling includes:
producing predictions on the unlabelled image dataset after the fully supervised segmentation model is finetuned through the co-heterogenous training and the ADA;
extracting 3D holes in tissue regions greater than 100 voxels;
creating a pseudo label for indicating a pathological region at each extracted hole, to obtain a "holes" dataset; and
finetuning the fully supervised segmentation model by replacing $L_{seg}$ with a segmentation loss obtained according to the "holes" dataset.

15. The product of claim 9, wherein the labelled image dataset includes a dataset with a number of curated and labelled V-phase liver images including CT scans and masks.

16. The product of claim 9, wherein the unlabelled image dataset includes a number of unlabelled multi-phase CTs from an uncurated clinical source.

17. A system for processing clinical three-dimensional image, comprising:
a processor,
a memory, containing computer program instructions that are configured to be executed by the processor to perform operations comprising:
training a fully supervised segmentation model using a labelled image dataset containing images for a disease at a predefined set of contrast phases or modalities, to allow a segmentation model to segment images at the predefined set of contrast phases or modalities;
finetuning the fully supervised segmentation model through co-heterogenous training and ADA using an unlabelled image dataset containing clinical multi-phase or multi-modality image data, to allow the segmentation model to segment images at contrast phases or modalities other than the predefined set of contrast phases or modalities; and
further finetuning the fully supervised segmentation model using domain-specific pseudo labelling to identify pathological regions missed by the segmentation model.

18. The system of claim 17, wherein training the fully supervised segmentation model using the labelled image dataset includes:
receiving a curated and labelled dataset of clinical three-dimensional images and masks;
selecting a PHNN framework; and
training, through a supervised learning, the PHNN framework using the curated and labelled dataset of clinical three-dimensional images and masks, to obtain the fully supervised segmentation model.

19. The system of claim 17, wherein the co-heterogenous training includes fusing hetero-modal learning with co-training to form a multi-modal learning for performing appearance-based learning from the unlabelled image dataset.

20. The system of claim 17, wherein the ADA includes training the fully supervised segmentation model to output predictions that follow a prediction distribution learned from the labelled image dataset by the segmentation model.

* * * * *